(12) United States Patent
Ruijters

(10) Patent No.: US 9,795,348 B2
(45) Date of Patent: Oct. 24, 2017

(54) MEDICAL VIEWING SYSTEM AND METHOD FOR GENERATING AN ANGULATED VIEW OF AN OBJECT OF INTEREST

(75) Inventor: Daniel Simon Anna Ruijters, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 474 days.

(21) Appl. No.: 13/695,641

(22) PCT Filed: Apr. 27, 2011

(86) PCT No.: PCT/IB2011/051819
§ 371 (c)(1),
(2), (4) Date: Nov. 1, 2012

(87) PCT Pub. No.: WO2011/138711
PCT Pub. Date: Nov. 10, 2011

(65) Prior Publication Data
US 2013/0051649 A1 Feb. 28, 2013

(30) Foreign Application Priority Data
May 3, 2010 (EP) .................................. 10161756

(51) Int. Cl.
*G06K 9/00* (2006.01)
*A61B 6/00* (2006.01)
(Continued)

(52) U.S. Cl.
CPC ............... *A61B 6/463* (2013.01); *A61B 6/12* (2013.01); *A61B 6/4441* (2013.01);
(Continued)

(58) Field of Classification Search
CPC .................. A61B 6/485; G06T 7/0012; G06T 2207/10121; G06T 2207/30101;
(Continued)

(56) References Cited

U.S. PATENT DOCUMENTS 5,371,778 A 12/1994 Yanof et al.
6,470,207 B1 * 10/2002 Simon et al. ................. 600/426
(Continued)

FOREIGN PATENT DOCUMENTS

DE 102008045276 A1 3/2010
JP 200338477 A 2/2003
(Continued)

OTHER PUBLICATIONS

Penney et al., A comparison of similarity measures for use in 2D-3D medical image registration, 1998, Medical Image Computing and Computer-Assisted Interventation, Lecture Notes in Computer Science vol. 1496, 1998, pp. 1153-1161.*

*Primary Examiner* — Vu Le
*Assistant Examiner* — Guillermo Rivera-Martinez

(57) ABSTRACT

In a medical viewing system having an X-ray image acquisition device a data processing unit is adapted for generating two different views on a three-dimensional image set, wherein a first view is corresponding to the viewing direction of the X-ray image acquisition device and a second view has a rotational offset to the first viewing direction. The first view may include live X-ray images, e.g. for monitoring a stent placement. The second view 10 supports a clinician to unambiguously judge whether ostia connection points may be blocked that are not clearly visible in anterior-posterior images.

23 Claims, 3 Drawing Sheets

(51) Int. Cl.
*A61B 6/12* (2006.01)
*A61B 90/00* (2016.01)
*A61B 34/10* (2016.01)

(52) U.S. Cl.
CPC ... *A61B 2034/107* (2016.02); *A61B 2090/365* (2016.02); *A61B 2090/367* (2016.02); *A61B 2090/376* (2016.02); *A61B 2090/3762* (2016.02)

(58) Field of Classification Search
CPC .................. G06T 7/0024; G06T 17/00; G06T 2207/20212; G06T 2219/2004
See application file for complete search history.

(56) References Cited

U.S. PATENT DOCUMENTS

| | | | |
|---|---|---|---|
| 6,711,433 B1* | 3/2004 | Geiger et al. | 600/431 |
| 7,117,027 B2 | 10/2006 | Zheng et al. | |
| 7,761,135 B2* | 7/2010 | Pfister et al. | 600/424 |
| 7,953,471 B2* | 5/2011 | Clayton et al. | 600/424 |
| 8,050,471 B2* | 11/2011 | Mielekamp et al. | 382/128 |
| 2004/0215071 A1* | 10/2004 | Frank et al. | 600/407 |
| 2005/0027193 A1* | 2/2005 | Mitschke et al. | 600/427 |
| 2005/0165292 A1* | 7/2005 | Simon et al. | 600/407 |
| 2007/0135707 A1* | 6/2007 | Redel et al. | 600/424 |
| 2008/0018645 A1 | 1/2008 | Dwyer et al. | |
| 2008/0292217 A1* | 11/2008 | Claus et al. | 382/304 |
| 2009/0290771 A1* | 11/2009 | Frank et al. | 382/128 |
| 2010/0246916 A1* | 9/2010 | Deuerling-Zheng et al. | 382/131 |

FOREIGN PATENT DOCUMENTS

| | | |
|---|---|---|
| WO | 2008047270 A1 | 4/2008 |
| WO | 2009040719 A2 | 4/2009 |

\* cited by examiner

MEDICAL VIEWING SYSTEM AND METHOD FOR GENERATING AN ANGULATED VIEW OF AN OBJECT OF INTEREST

FIELD OF THE INVENTION

The invention relates to the field of medical imaging. In particular, the invention relates to a medical viewing system and a method for generating an angulated view of an object of interest.

BACKGROUND OF THE INVENTION

Abdominal aortic aneurysms may be treated minimally-invasively by endovascular aneurysm repair, for example by placement of abdominal aortic aneurysm stentgrafts (in the following referred to as "stents"), which is placed by means of percutaneous catheterization. During placement of stents it is important that the ostias of the renal arteries are not blocked by a placed stent so that the blood flow to the kidneys is not obstructed. Stent placement may usually be accomplished by a minimal invasive treatment in the form of forwarding the stent within the artery to the desired location and expanding it there. It is widespread to monitor this procedure and guide the clinician for example by means of an X-ray image acquisition apparatus, where actual X-ray images obtained by the image acquisition device, for example of a C-arm type, are overlaid onto a previously obtained image with a contrast agent present in the respective vessels.

Unfortunately, the exact connection points of renal arteries to the aorta are not always visible in one view with a fixed viewing angle. This is particularly the case when the connection points are located at the back of the aorta when a standard anterior-posterior-projection is used. As a consequence, forwarding a stent to its desired location in an aorta may necessitate multiple manual changes of viewing directions of the respective examination apparatus in order to prevent the blocking of renal arteries.

WO 2008/047270 A1 shows a method for displaying images of an object under examination, wherein displayed three-dimensional images are combined with displays of two-dimensional images corresponding to a selected projection angle.

SUMMARY OF THE INVENTION

The main drawback of known methods for generating views of objects of interest, especially for the purpose of guiding intravascular devices lies in the necessity of changing the viewing directions multiple times for being able to unambiguously judge whether the device is positioned properly or not.

It would therefore be advantageous to suggest a medical viewing system and a method for providing a view of an object of interest that is capable of simplifying and streamlining the monitoring of ostia of branching vessels from an aorta or the such, especially when navigating and deploying intravascular devices.

To better address one or more of these concerns, in a first aspect of the invention there is provided a medical viewing system comprising an X-ray image acquisition device for providing a view of an object of interest.

For the following description of the invention it is assumed that a three-dimensional reconstruction of the pathological structure to be examined is present. Usually, this three-dimensional reconstruction may pre-operatively be obtained through one or several methods well known for a person skilled in the art. This reconstruction may be realized on the basis of X-ray images acquired with a C-arm X-ray image acquisition device from several directions of view. Alternatively, a CT scan or the such for diagnostic purposes and treatment planning may be used for this purpose. Nevertheless, the subject of the present invention is not limited to the type of acquiring a three-dimensional representation of a structure.

Assuming the visibility of the pathologic anatomical structure in the three-dimensional dataset, according to a first aspect the medical viewing system comprises a data processing unit and an output unit, wherein the medical viewing system is adapted for receiving at least a part of a three-dimensional data set representing an anatomical structure and live X-ray images.

The data processing unit is adapted for generating a first two-dimensional projection of the three-dimensional data set onto a first plane according to a predetermined first viewing angle. The data processing unit is further adapted for generating a second two-dimensional projection of the three-dimensional data set onto a second plane according to a second viewing angle. Still further, the data processing unit is adapted for overlaying the live X-ray images onto the first two-dimensional projection after a registration process, which registration process may be realized as any common registration process that is well known to a person skilled in the art. The first projection together with the overlaid X-ray images and the second projection are provided as a set of viewing image data and preferably as a stream of viewing image data.

The output unit is adapted for outputting the viewing image data to a display device, a further processing unit, a storage unit or the such.

The gist of the invention lies in displaying two different views onto an object of interest represented by a three-dimensional image data at two distinct viewing angles. The second two-dimensional projection may be called an "angulated view", wherein the first two-dimensional projection may be referred to as "first view". A rotational offset of the angulated view to the first view may be set to a constant angle and rotation axis or can be chosen and altered by the user. In this way, a virtual bi-plane view can be created that shows the anatomy of interest from a different fixed angle than the X-ray image. This complements the anatomy information in the live X-ray image.

Using a C-arm image acquisition device as the X-ray image acquisition device of the medical viewing system according to the invention allows the generation of three-dimensional images based on two-dimensional X-ray images from varying directions and the further conversion in a known manner into a three-dimensional X-image reconstruction. To display the three-dimensional image data from a given viewing angle onto a two-dimensional display device a projection of the three-dimensional image data onto a viewing plane is conducted. The relation between the orientation of the actual viewing plane and the orientation of the C-arm image acquisition device may be variable and it is widespread to use at least two different display modes in such medical viewing systems. A first display mode may be a "follow C-arc" mode, where the orientation of the viewing plane follows the C-arm geometry viewing incidence. Thereby, when the C-arm is moved the viewing plane always corresponds to the viewing angle of the C-arm. On the other hand a "three-dimensional automatic position control" mode, which can be regarded as the opposite of the follow-C-arc mode, moves the C-arm in relation to the orientation of the viewing plane. Thereby, a live X-ray image, created from the given incidence, should depict the same scene as is displayed through the viewing plane. This mode can be used to plan a view, without actually radiating or injecting contrast medium and to evaluate the three-dimensional morphology for a given viewing incidence. According to the invention it may be advantageous to operate the medical viewing system according such that the first view corresponds to the follow C-arc mode.

According to an exemplary embodiment of the invention the angulated view is inclined to the first view at a predetermined offset angle, wherein the rotation axis is the head-feet axis of the patient. This offset angle may lie in a range of 30° to 150° in order to allow the judging of approach to connecting points of ostia or the such. Thereby, it is not necessarily required to change the viewing direction through triggering input means since the region of interest is always monitored from two different viewing directions.

According to an exemplary embodiment of the invention the rotation axis about which the offset angle is defined is a left-right-axis of the patient. This offset angle may also lie in a range of 30° to 150° in order to allow the judging of approach to connecting points.

According to an exemplary embodiment the offset range is given to 90° which is beneficial for the placement of abdominal aortic aneurysm stents.

According to an exemplary embodiment the data processing unit is adapted to generate a viewing image data where the first view and the angulated view are positioned side by side and in the same scale.

According to an exemplary embodiment the data processing unit is further adapted for generating at least one reference line that extends from the most advanced edge of an intravascular device in the first view in a horizontal manner over the angulated view. Thereby the clinician is supported in judging the position of the stent or other intravascular device in relation to any important reference points, such as connection points of ostias. The generation of the reference line may be conducted by comparing the live X-ray image with previous live X-ray images to detect the intravascular device and its forwarding direction. Since such a device usually comprises a clear contrast the outline of this device may be detected rather easily. As an alternative, the clinician may define an element in a live X-ray image, wherein the motion of this element may then be monitored by the data processing unit in order to link the reference line to this element during obtaining subsequent X-ray images.

To better address one or more of the above mentioned concerns, in a second aspect of the invention there is provided a method for generating an angulated view onto an object of interest, which method basically comprises the steps of selecting a viewing direction, moving the X-ray image acquisition device to correspond this viewing direction, obtaining X-ray images, generating a first view corresponding to the selected viewing angle, overlaying X-ray images, generating an angulated view represented by an offset angle to the first viewing direction and further optionally generating reference lines to mark an intravascular device in the angulated view.

In another exemplary embodiment of the present invention a computer program or a computer program element is provided, which computer program element is a part of a computer program adapted for controlling a device, e.g. a medical viewing system according to one of the above-described aspects, which, when being executed by a processing unit, is adapted to perform corresponding method steps according to the invention.

The computer program element may therefore be stored on a computing unit, a calculating device or an electronic device, which may also be part of an embodiment of the present invention. The computing unit may be adapted to perform or initiate a performing of method steps associated with the above-described device. Moreover, it may be adapted to operate the components of the above-described device. A computer program element may be loaded into a working memory of a data processor, which data processor may thus be equipped to carry out the method according to the invention.

This exemplary embodiment of the invention covers both, a computer program element is adapted for using the invention right from the start and a computer program element that is adapted for using the invention through being integrated by means of an update to turn an existing program into a program that uses the invention.

Further, the computer program element may also be able to provide all necessary steps to fulfill the steps of an exemplary embodiment of the method according to the invention as described above.

According to a further exemplary embodiment of the present invention, a computer readable medium, such as a CD-ROM or the like, is presented wherein the computer readable medium has a computer program element stored on it, which computer program element is described by the preceding section.

However, the computer program element may also be presented over a network like the World Wide Web and may be downloadable into the working memory of a data processor from such a network.

According to a further exemplary embodiment of the present invention, a medium for making a computer program element available for downloading is provided, which computer program element is adapted to perform a method according to one of the previously described embodiments of the invention.

Additional embodiments deriving from view generation method steps are conceivable and are understood to be included in the invention described in this disclosure.

It has to be noted that exemplary embodiments of the invention are described with reference to different subject matters. In particular, some exemplary embodiments are described with reference to method type claims whereas other embodiments are described with reference to the apparatus type claims.

It has to be noted that exemplary embodiments of the invention are described with reference to different subject matters. In particular, some exemplary embodiments are described with reference to apparatus type claims whereas other exemplary embodiments are described with reference to method type claims. However, a person skilled in the art will gather from the above and the following description that, unless otherwise notified, in addition to any combination of features belonging to one type of subject matter also any combination between features relating to different subject matters, in particular between features of the apparatus type claims and features of the method type claims, is considered to be disclosed with this application. However, all features can be combined providing synergetic effects that are more than the simple summation of the features.

DETAILED DESCRIPTION OF EMBODIMENTS

Figure 1:
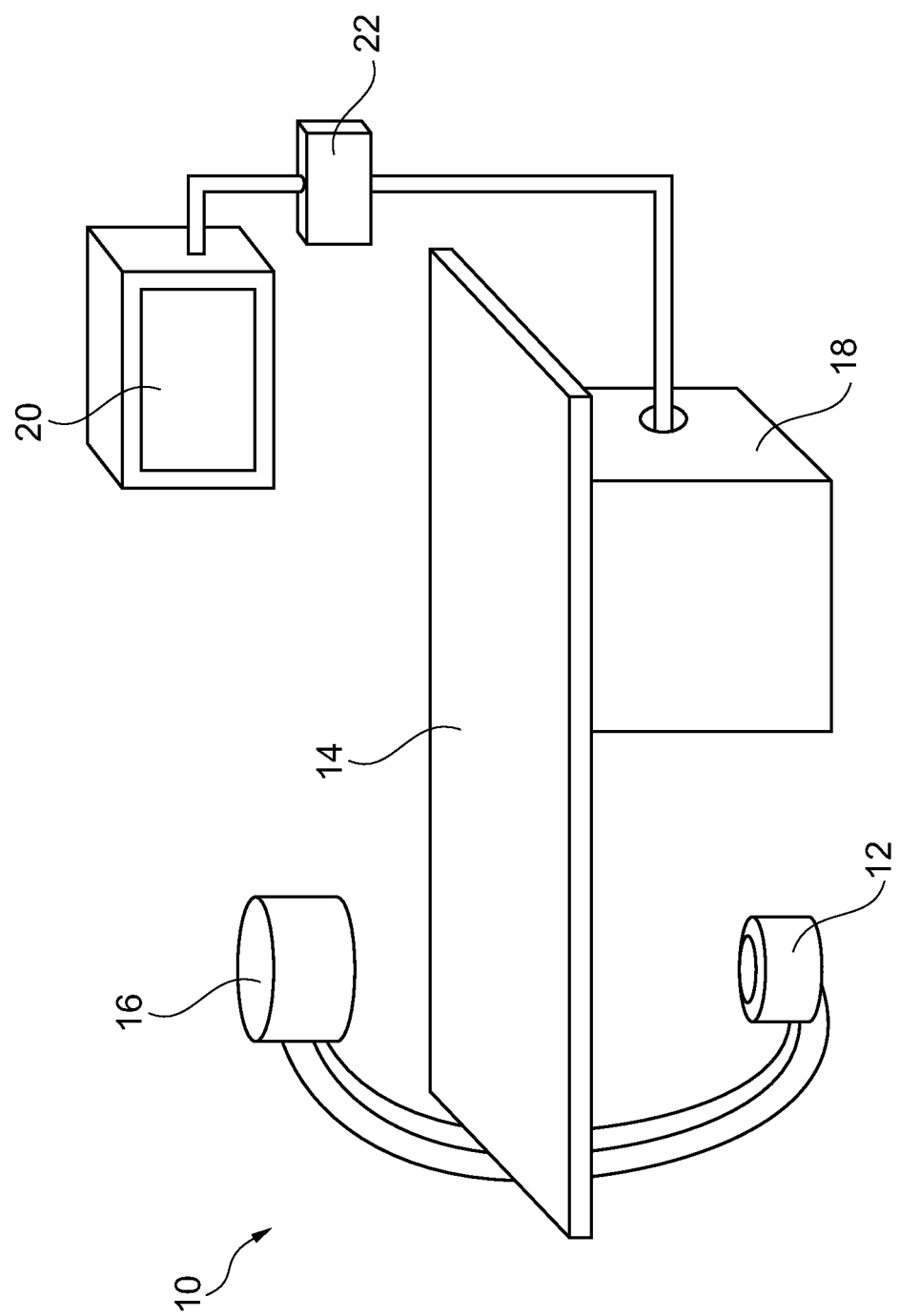
FIG. 1 shows a medical viewing system according to the present invention.

FIG. 1 schematically shows a medical viewing system for generating an angulated view of an object of interest.

The medical viewing system 10 comprises an X-ray image acquisition device with a source of X-ray radiation 12 provided to generate X-ray radiation. A table 14 is provided to receive an object to be examined. Further, an X-ray image detection module 16 is located opposite the source of X-ray radiation 12. During the radiation procedure, the examined object is located between the source of X-ray radiation 12 and the detection module 16. The latter sends data to a data processing unit 18, which is connected to both the X-ray image detection module 16 and the X-ray radiation source 12. The data processing unit 18 is exemplarily located underneath the table 14 for saving space within the examination room. It is clear that it could also be located at a different place, such as in a different room or a different laboratory. Furthermore, an output unit 20 is exemplarily equipped with a display and therefore may be arranged in the vicinity of the table 14 for displacing information to the person operating the medical viewing system, which can be a clinician such as a cardiologist or a cardiac surgeon. Preferably, the display is movably mounted to allow for an individual adjustment depending on the examination situation. Also, an interface unit 22 is arranged to input information by the user.

It is not necessary to use a standalone output unit 20, it may also be possible to include the output unit 20 in the data processing unit 18, where the overlaying and combining process is conducted and provided at suitable output ports for further purposes.

Basically, the image detection module 16 generates images by exposing this subject to X-ray radiation, wherein said images are further processed in the data processing unit 18. It is noted that the example shown is of a so-called C-type X-ray image acquisition device. The X-ray image acquisition device comprises an arm in form of a C where the detection module 16 is arranged at one end of the C-arm and the source of X-ray radiation 12 is located at the opposite end of the C-arm. The C-arm is movably mounted and can be rotated around the object of interest located on the table 14. In other words, it is possible to acquire images with different directions of view.

The data processing unit 18 may be adapted to conduct the method according to the invention and thus can be considered as or comprise the data processing unit for generating an angulated view on an object of interest. Thereby, a data processor and preferably a storage means for storing the optimal viewing directions is provided as well as a related software that leads one program element for generating an angulated view of an object of interest according to exemplary embodiments of the above-described method. The software can be transferred into the data processing unit 18 by means of a computer-readable medium or through a network and may be realized as a complete new operating system or an update.

Figure 2:
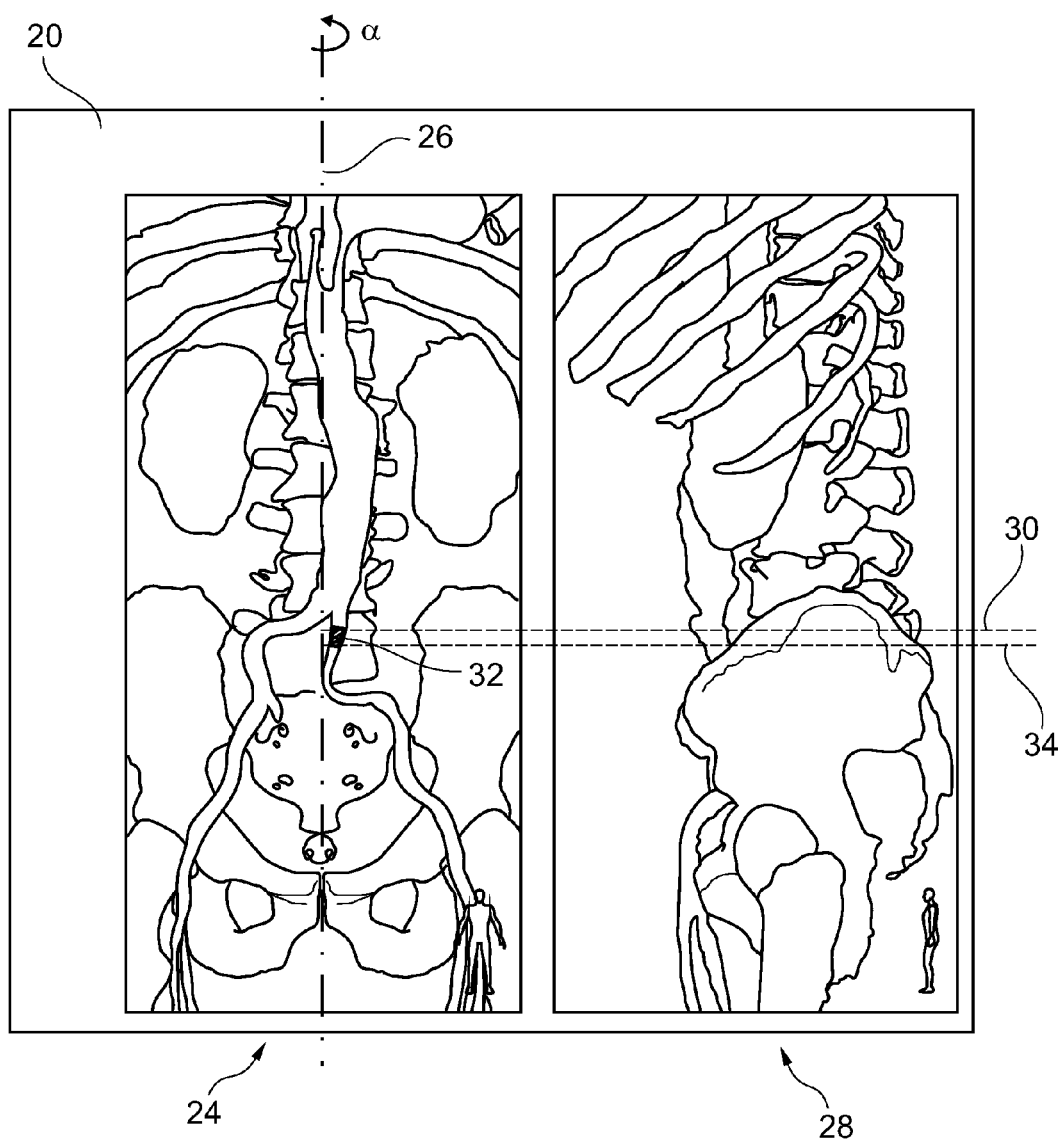
FIG. 2 shows a generated view of an object of interest with a first view and an angulated view.

FIG. 2 shows an exemplarily generated view of an object of interest as it may be provided at the output unit 20 of the medical viewing system according to the invention. On the left side a first view 24 is shown that corresponds to the viewing direction of the X-ray image acquisition device. During the placement of intravascular devices this first view 24 may not be sufficient for judging whether the intravascular devices may obstruct connection points of ostias or the such. Therefore, a rotational axis 26 is defined about which the viewing direction of an angulated view 28 may be rotated up to an offset angle α. Exemplarily, the rotational axis 26 is corresponding with a head-feet axis of a patient on the table 14. It is to be understood that also another definition of rotational axis 26 may be used, for example a left-right-axis.

FIG. 2 shows the first view 24 and the angulated view 28 in a side by side manner, wherein the offset angle α is exemplarily set to 90° around the rotational axis 26. Both views 24 and 28 have the same scale.

Let vector $\vec{v}$ represent the viewing direction of the X-ray image acquisition device in the space of a three-dimensional representation of an object of interest, especially a patient's anatomy of interest. The viewing direction of the angulated view 28 may then be described by the following equation:

$$\vec{v}' = R\vec{v}$$

wherein $\vec{v}'$ represents the viewing direction of the angulated view 28, and matrix R represents a 3 by 3 angulation matrix representing a rotational offset α, which matrix may be defined as follows:

$$R = \begin{pmatrix} c + t \cdot a_x^2 & t \cdot a_x \cdot a_y + s \cdot a_z & t \cdot a_x \cdot a_z - s \cdot a_y \\ t \cdot a_x \cdot a_y - s \cdot a_z & c + t \cdot a_y^2 & t \cdot a_y \cdot a_z + s \cdot a_x \\ t \cdot a_x \cdot a_z + s \cdot a_y & t \cdot a_y \cdot a_z - s \cdot a_x & c + t \cdot a_z^2 \end{pmatrix}$$

with $\vec{a} = (a_x, a_y, a_z)^T$ being the rotational axis 26;
$c = \cos(\alpha)$;
$s = \sin(\alpha)$ and
$t = 1 - c$.

The data processing unit 18 is adapted for generating the angulated view 28 together with the first view 24. Any change of the vector $\vec{v}$ will therefore immediately lead to a change of the viewing direction of the angulated view 28.

Additionally, it may be advantageous to generate a reference line 30 that corresponds to a most forwarded edge of an intravascular device 32 that is being forwarded within a vessel. The reference line 30 extends over the first view 24 and the angulated view 28 so that a clinician quickly recognizes when the intravascular device may be in a position that obstructs a connection point of a vessel.

It may additionally be advantageous to generate a reference line 34 of a least forwarded edge of the intravascular device in order to mark the section of a vessel occupied by the intravascular device within the angulated view.

Figure 3:
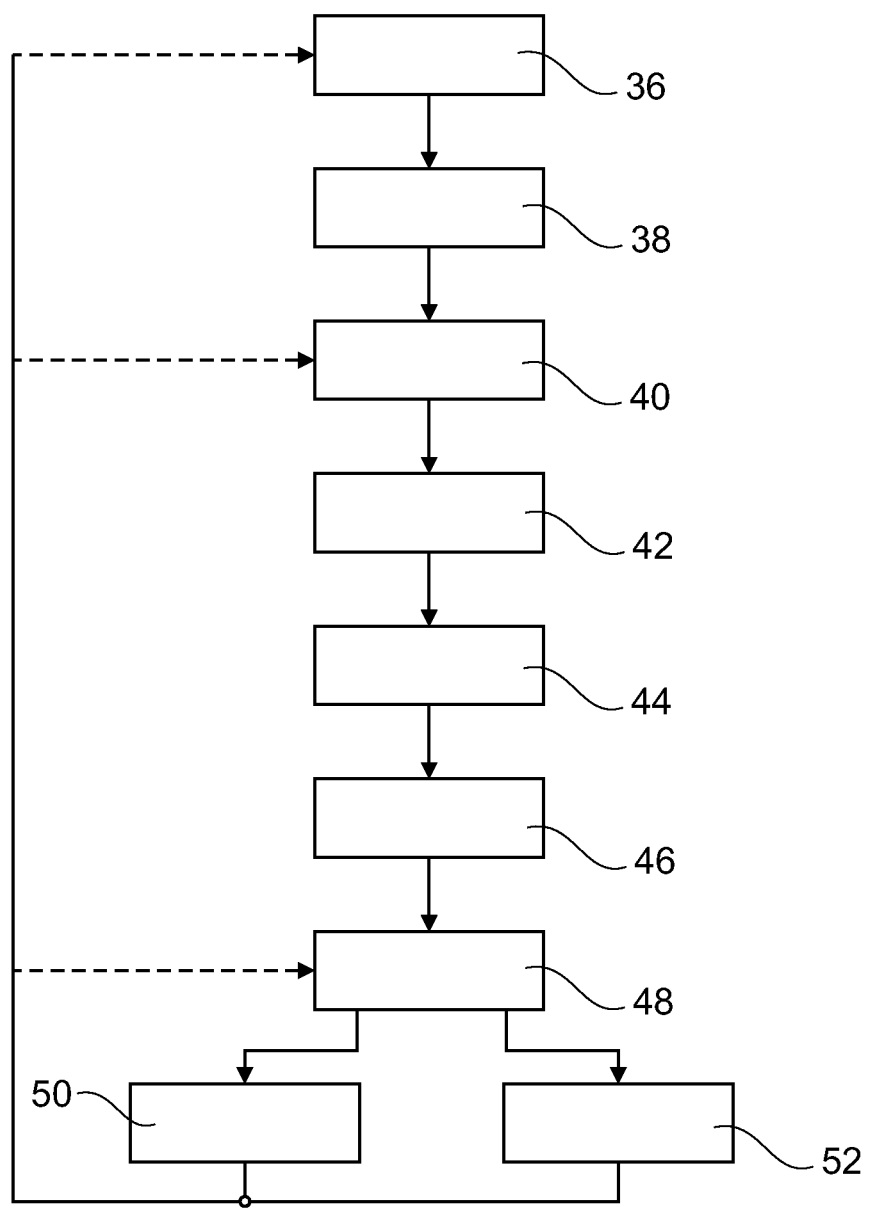
FIG. 3 shows a method according to the invention in a schematic block-oriented diagram.

In FIG. 3 the method according to the present invention is further described in detail. After selecting 36 a viewing direction and moving 38 the X-ray image acquisition device to correspond this viewing direction X-ray images are obtained 40. A first projection of a three-dimensional data set corresponding to the selected viewing direction is generated 42 and the obtained X-ray images are overlaid 44 with this first view.

In order to support the first view an angulated view is generated 46, which angulated view is represented by a two-dimensional projection of the three-dimensional data set based on an angulated viewing direction, wherein the selected viewing direction vector of the X-ray image acquisition device and an angulated viewing direction vector enclose an offset angle α. In order to adjust the angulated view the offset angle α may be altered 48.

For improving the connection between the first view and the angulated view at least one first reference line 30 may be generated 50, wherein the reference line 30 may correspond to a most forwarded edge of an intravascular device 32. Further, at least one second reference line 34 may be generated 52, which reference line 34 may correspond to a least forwarded edge of the intravascular device 32.

The method according to the invention can then be repeated, beginning with selecting 36 a viewing angle, obtaining 40 X-ray images, altering 48 the offset angle or any other method step.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage.

A computer program may be stored and/or distributed on a suitable medium, such as an optical storage medium or a solid state medium supplied together with or as part of other hardware, but may also be distributed in other forms, such as via the internet or other wired or wireless telecommunication systems.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

Any reference signs in the claims should not be construed as limiting the scope.

LIST OF REFERENCE SIGNS

10 Medical viewing system
12 Source of X-ray radiation
14 Table
16 X-ray detection module
18 Data processing unit
20 Output unit
22 Interface unit
24 First view
26 Rotational axis
28 Angulated view
30 First reference line
32 Intravascular device
34 Second reference line
36 Selecting a viewing direction
38 Moving X-ray image acquisition device
40 Obtaining X-ray images
42 Generating first projection
44 Overlaying X-ray images
46 Generating angulated view
48 Altering offset angle
50 Generating a first reference line
52 Generating a second reference line

The invention claimed is:

1. A medical viewing system comprising:
    an X-ray image acquisition device with a source of radiation and an X-ray image detection module;
    an image processor; and
    a display;
    wherein the image processor is configured for:
        retrieving a three-dimensional image data set, generating a first two-dimensional projection of the three-dimensional image data set corresponding to a first viewing direction; and
        overlaying X-ray images onto the first two-dimensional projection constituting a first view;
    wherein the image processor is configured for generating a second two-dimensional projection of the three-dimensional image data set corresponding to a second viewing direction constituting a second view, wherein a first viewing direction vector and a second viewing direction vector enclose an offset angle α,
    wherein the display is configured for outputting a combination of the first view and the second view with the same scale in a side by side manner, and
    wherein the image processor is configured for generating at least one reference line extending on the first view and the second view and corresponding to an edge of an intravascular device to be monitored by the medical viewing system.

2. The medical viewing system according to claim 1, wherein the offset angle α is measured as a rotational angle about a head-feet-axis of a patient.

3. The medical viewing system according to claim 2, wherein the offset angle α is in a range between 30 and 150°.

4. The medical viewing system according to claim 2, wherein the offset angle α is 90°.

5. A method for generating an angulated view of an object of interest, comprising the acts of:
    retrieving a three-dimensional image data set;
    generating a first two-dimensional projection of the three-dimensional data set corresponding to a first viewing direction, constituting a first view;
    overlaying X-ray images onto the first two-dimensional projection constituting a first view;
    generating a second two-dimensional projection of the three-dimensional data set corresponding to a second viewing direction constituting the angulated view, wherein a first viewing direction vector and a second viewing direction vector enclose an offset angle α;
    outputting a combination of the first view and the angulated view with the same scale in a side by side manner; and
    generating at least one reference line extending on the first view and the angulated view and corresponding to an edge of an intravascular device to be monitored by a medical viewing system.

6. A non-transitory computer-readable medium embodying a program for medical view, said program having instructions executable by a data processing unit for performing a plurality of acts, among said plurality there being the acts of:

retrieving a three-dimensional image data set;
generating a first two-dimensional projection of the three-dimensional data set corresponding to a selected first viewing direction, constituting a first view;
overlaying X-ray images onto the first two-dimensional projection constituting a first view;
generating a second two-dimensional projection of the three-dimensional data set corresponding to a second viewing direction constituting a second view, wherein a first viewing direction vector and a second viewing direction vector enclose an offset angle α;
outputting a combination of the first view and the second view with the same scale in a side by side manner; and
generating at least one reference line extending on the first view and the second view and corresponding to an edge of an intravascular device to be monitored by a medical viewing system.

7. The medical viewing system of claim 1, said generating of said line including finding, by said image processor, said intravascular device automatically, without need for user intervention.

8. The medical viewing system of claim 7, said generating of said line including finding, by said image processor, said edge automatically, without need for user intervention.

9. The medical viewing system of claim 8, said edge being a most forwarded edge of said intravascular device that is being forwarded within a vessel.

10. The medical viewing system of claim 1, configured for performing the monitoring automatically, without need for user intervention.

11. The medical viewing system of claim 1, said outputting including outputting, as said second view, said three-dimensional image data set from a viewing angle corresponding to said second viewing direction.

12. The medical viewing system of claim 11, said outputting including outputting, as said first view, said three-dimensional image data set from a viewing angle corresponding to said first viewing direction.

13. The medical viewing system of claim 1, said image processor being configured for the generating of said first two-dimensional projection onto a first plane according to a predetermined first viewing angle corresponding to said first viewing direction.

14. The medical viewing system of claim 13, said image processor being configured for the generating of said second two-dimensional projection onto a second plane according to a predetermined second viewing angle corresponding to said second viewing direction.

15. The medical viewing system of claim 1, further comprising a user interface by which said offset angle α is user adjustable.

16. The medical viewing system of claim 1, said overlaying being dynamically responsive to said generating of said first two-dimensional projection.

17. The medical viewing system of claim 16, said outputting being dynamically responsive to said overlaying.

18. The system of claim 1, an image from among said X-ray images to be overlaid including a depiction of an anatomical structure.

19. The system of claim 18, said data set comprising an image of said anatomical structure depicted.

20. The system of claim 1, said outputting entailing presenting, as horizontally aligned, said first view with respect to said second view.

21. The computer readable medium of claim 6, an image from among said X-ray images to be overlaid including a depiction of an anatomical structure.

22. The computer readable medium of claim 6, said outputting entailing presenting, as horizontally aligned, said first view with respect to said second view.

23. The system of claim 1, wherein said image processor is an image processing unit.

* * * * *